(12) United States Patent
Sugimoto

(10) Patent No.: US 8,520,218 B2
(45) Date of Patent: Aug. 27, 2013

(54) MEASURING METHOD OF REFRACTIVE INDEX AND MEASURING APPARATUS OF REFRACTIVE INDEX

(75) Inventor: Tomohiro Sugimoto, Minamisaitama-gun (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 13/230,231

(22) Filed: Sep. 12, 2011

(65) Prior Publication Data

US 2012/0069350 A1 Mar. 22, 2012

(30) Foreign Application Priority Data

Sep. 16, 2010 (JP) .................................. 2010-207647
Jun. 27, 2011 (JP) .................................. 2011-141527

(51) Int. Cl.
*G01N 21/41* (2006.01)
*G01N 21/43* (2006.01)

(52) U.S. Cl.
USPC .......................................... 356/517; 356/128

(58) Field of Classification Search
USPC ......... 356/73.1, 124–128, 131, 517, 512–516
See application file for complete search history.

(56) References Cited

U.S. PATENT DOCUMENTS

2010/0165355 A1* 7/2010 Kato .............................. 356/517

FOREIGN PATENT DOCUMENTS

| JP | 02-008726 A | 1/1990 |
| JP | 11-344313 A | 12/1999 |

* cited by examiner

*Primary Examiner* — Gregory J Toatley
*Assistant Examiner* — Hina F Ayub
(74) *Attorney, Agent, or Firm* — Rossi, Kimms & McDowell LLP

(57) ABSTRACT

A measuring method includes measuring a sum of an optical path length of a test object and a first medium in a first container, introducing light into an area that includes the first medium but does not include the test object and measuring the optical path length of the first medium, measuring a sum of the optical path length of the test object and a second medium in a second container, the second medium having a refractive index different from that of the first medium, introducing the light into an area that includes the second medium but does not include the test object and of measuring the optical path length of the second medium, and calculating a refractive index of the test object based on the measured optical path lengths and an actual distance of an optical path for which each optical path length is measured.

13 Claims, 5 Drawing Sheets

MEASURING METHOD OF REFRACTIVE INDEX AND MEASURING APPARATUS OF REFRACTIVE INDEX

BACKGROUND OF THE INVENTION

1. Field of the Invention

The present invention relates to a measuring method of a refractive index and a measuring apparatus of a refractive index.

2. Description of the Related Art

Japanese Patent Laid-Open No. ("JP") 11-344313 proposes a method for fixing a test object between two transparent plates via intervals among them, for measuring an optical path length between the transparent plates, an optical path length between the transparent plate and the test object, and an optical path length in the test object, and for calculating a refractive index of the test object based on the measurement results. JP 02-008726 proposes a method for measuring a refractive index of a test object by immersing a glass sample having a known refractive index and a known shape and the test object in each of two types of matching oils having different refractive indices.

The method disclosed in JP 11-344313 has difficulties in measurements when the test object, such as a lens having a curved surface, decenters or tilts relative to the optical axis, and needs time-consuming strict centering or slope adjustments. Otherwise, measured value would contain errors due to the influence of the curvature of the reflected surface.

The method disclosed in JP 02-008726 needs time-consuming adjustments of the refractive index of the matching oil due to blending of different types of oils. In addition, in measuring a transmitted wavefront of the test object having a high refractive index in accordance with the method of JP 02-008726, a detector can output only a weak signal and the measuring precision becomes low, because the matching oil having a high refractive index has a low transmittance.

SUMMARY OF THE INVENTION

The present invention provides a measuring method and a measuring apparatus, which can provide quick and highly precise measurements of a refractive index of a test object.

A measuring method according to the present invention includes a first measuring step of introducing light onto a test object and a first medium arranged in a first container and of measuring a sum of an optical path length of the test object and an optical path length of the first medium, a second measuring step of introducing the light onto an area that includes the first medium but does not include the test object and of measuring the optical path length of the first medium, a third measuring step of introducing the light onto the test object and a second medium arranged in a second container and of measuring a sum of the optical path length of the test object and an optical path length of the second medium, the second medium having a refractive index different from that of the first medium, a fourth measuring step of introducing the light into an area that includes the second medium but does not include the test object and of measuring the optical path length of the second medium, and a calculating step of calculating a refractive index of the test object based on the optical path lengths measured in each measuring step and an actual distance of an optical path for which each optical path length is measured in each measuring step.

Further features of the present invention will become apparent from the following description of exemplary embodiments with reference to the attached drawings.

DESCRIPTION OF THE EMBODIMENTS

A description will be now given of embodiments according to the present invention with reference to the accompanying drawings.

First Embodiment

Figure 1:
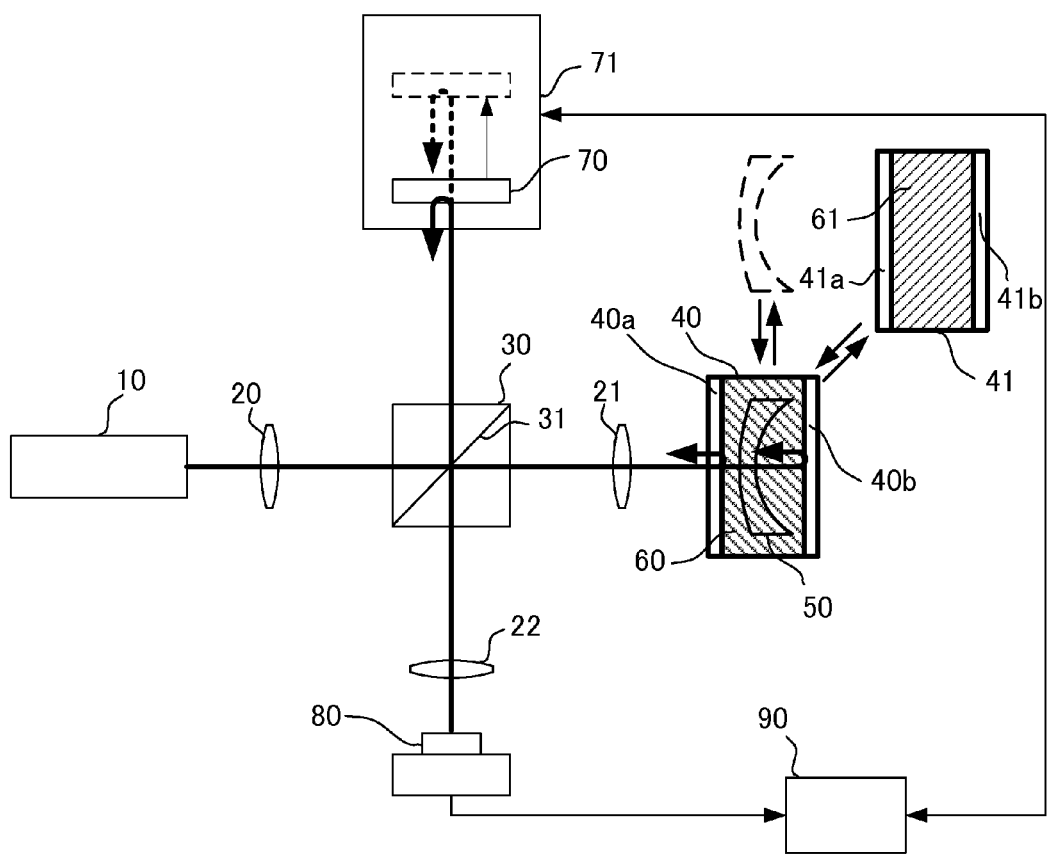
FIG. 1 is a block diagram of a measuring apparatus according to a first embodiment.

FIG. 1 is a block diagram of a measuring apparatus (low-coherence interferometer) according to a first embodiment. The measuring apparatus of this embodiment finds a refractive index of a test object by measuring a sum of an optical path length of the test object and an optical path length of each of two types of media in which the test object is arranged and an optical path length of each medium from which the test object is removed. The test object of this embodiment is a lens having a negative power, but the measuring apparatus can measure refractive indices of any test objects and the test object may be a lens or a flat plate as long as the test object is a refracting optical element.

The measuring apparatus includes a light source 10, an interference optical system, a mirror (reference unit) 70, a container, such as a first container 40 and a second container 41, configured to house a medium and a test object, a detector 80, and a computer 90, and is configured to measure the refractive index of the object 50. The measuring apparatus of this embodiment can measure a group refractive index, a phase refractive index, and a thickness of the test object. The light source 10, the interference optical system, the mirror 70, the container, and the detector 80 constitute a measuring unit.

The light source 10 is a light source, such as a super luminescent diode (SLD), configured to emit low coherent light having a broad wavelength band (or broad spectrum). A coherence length $\Delta z$ of a broadband light source can be expressed as follows:

$$\Delta z = \frac{2\ln 2}{\pi} \frac{\lambda_c^2}{\Delta \lambda} \qquad \text{Expression 1}$$

Herein, $\lambda_c$ denotes a central wavelength of the broadband light source, and $\Delta\lambda$ is a spectral bandwidth. For highly precise measurements of the optical path length, $\Delta z$ smaller than 30 µm may be suitable. For example, where $\lambda_c$=1.310 µm and $\Delta\lambda$=0.050 µm, $\Delta z$~15 µm is met.

The interference optical system is configured to split a light flux from the light source 10 into two light fluxes, and to guide one light flux to the test object and the other light flux to a reference unit. The interference optical system enables test light reflected by the container configured to house the test object 50 (on its surfaces sandwiching the test object) and the reference light reflected by the reference unit to superimpose onto each other and interfere each other, and to guide an interference light to the detector 80. The interference optical system includes a (collimator) lens 20, a beam splitter 30, and (condenser) lenses 21, 22.

The lens 20 is arranged between the light source 10 and the beam splitter 30, and configured to turn a light flux from the light source 10 into a parallel light flux. The lens 21 is arranged between the beam splitter 30 and the container, and configured to condense the light from the beam splitter 30 onto the test object 50. The lens 22 is arranged between the beam splitter 30 and the detector 80, and configured to condense the interference light from the beam splitter 30 onto the detector 80.

The beam splitter 30 includes, for example, a cubic half-mirror, and its interface (bonding surface) 31 reflects part of the light from the light source 10 in the 90° upper direction and transmits remaining light. The reflected light is reflected on the upper mirror 70 in FIG. 1, and the transmitted light transmits through the interference 31 and travels to the container on the right side in FIG. 1.

The interface (bonding surface) 31 of the beam splitter 30 transmits part of the reference light from the mirror 70 and reflects the remaining light to the light source side. In addition, the interface (bonding surface) 31 of the beam splitter 30 reflects part of the test light from the container in 90° downward direction and transmits the remaining light to the light source side. As a result, part of the reference light and part of the test light interfere with each other and form interference light, and the interference light is emitted to the detector 80.

The first container 40 houses a first medium 60, such as air, and the test object 50. In this embodiment, an area in the first container in which the first medium 60 and the test object 50 are arranged may be part or whole of the capacity of the first container 40.

The test object 50 can be inserted into and ejected from the first container 40 as illustrated by dotted arrows. The first container 40 can be automatically or manually exchanged with the second container 41 configured to house a second medium 61, such as oil, having a refractive index different from that of the first medium 60. The test object 50 can also be inserted into and ejected from the second container 41 as illustrated by the dotted arrow.

A side 40a of the first container 40 in the light transmitting direction is made of a transparent material, such as glass. Another side 40b of the first container 40 in the light transmitting direction may be made of a transparent material or an opaque material, such as a mirror. The second container 41 is similarly configured. The test light is the light that is reflected on the container or the test object.

The mirror 70 is supported by the stage 71 and configured to move along the optical path. A moving amount of the mirror 70 is measured by a length measuring system (not illustrated), such as an encoder and a laser length measuring machine, and controlled by the computer 90 that serves as a processor and calculator. The mirror 70 and the stage 71 will be collectively referred to as a "movable mirror" hereinafter. The reference light is light made as a result of that the reflected light from the beam splitter 30 is reflected by the mirror 70.

The detector 80 detects a light intensity of the interference light from the beam splitter 30, and includes a photodiode or the like.

The computer 90 includes a CPU and serves as a calculator configured to calculate the refractive index of the test object based on the detection result (measurement result) of the detector 80, as well as a controller configured to control the moving amount of the movable mirror. The computer 90 may further control turning on and off of the light source 10, inserting the test object 50 into and ejecting the test object 50 from of the first container 40 or the second container 41, and a replacement between the first container 40 and the second container 41.

Figure 2:
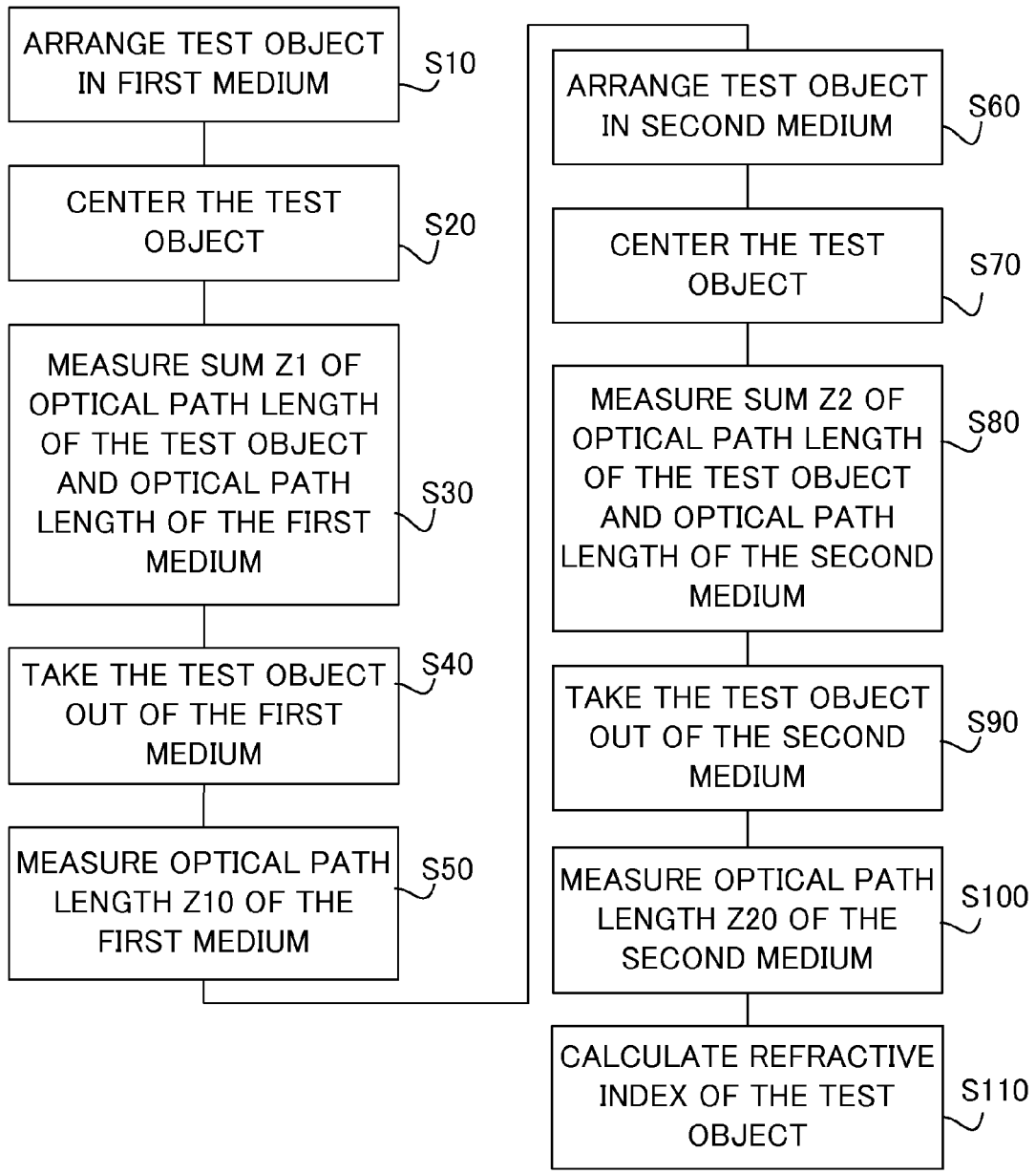
FIG. 2 is a flowchart for explaining a procedure of calculating a refractive index of a test object using the measuring apparatus illustrated in FIG. 1 according to the first embodiment.

FIG. 2 is a flowchart for explaining a procedure of calculating the refractive index of the test object 50, and "S" stands for the step.

Initially, as illustrated in FIG. 1, the first medium 60 is filled in the first container, and the test object 50 is arranged in the first medium (S10).

Next, the test object 50 is centered relative to the optical axis (S20). For example, a light scattering member, such as a screen, is arranged behind the first container 40 (or on the side opposite to the light source via the container), and the test object 50 is centered so that light positions accord with each other on the screen between when the test object 50 is arranged in the medium and when the test object 50 is not arranged in the medium. An image pickup element, such as a CCD, may be arranged instead of the screen. When the side 40b is opaque, the side 40b may serve as the screen.

Next follows a first measuring step of introducing the light into the test object 50 and the first medium 60 arranged in the first container and of measuring a sum Z1 of an optical path length of the test object 50 and an optical path length of the first medium 60 (S30). The light emitted from the light source 10 is collimated by the lens 20, and then split into the transmitting light and reflected light by the beam splitter 30. Part of the reflected light transmits through the beam splitter 30, passes the lens 22, and reaches the detector 80.

The transmitting light passes the lens 21, and enters the medium and the test object 50 in the container. This light is partially reflected on a front surface and a back surface of the side 40a, on a front surface and a back surface of the test object 50, and a front surface and a back surface of the side 40b. If the side 40b is made of an opaque material, the light is reflected only on its front surface. Herein, the front surface means a surface on the side close to the light source 10, and the back surface means a surface distant from the light source 10.

FIG. 1 illustrates the light reflected on the back surface of the side 40a and the light reflected on the front surface of the side 40b using arrows. These reflected beams pass the lens 21 again and reach the beam splitter 30. Thereafter, part of the light is reflected on the beam splitter 30, passes the lens 22, and reaches the detector 80.

The interference between the test light and the reference light sporadically occurs as the movable mirror moves, and is detected by the detector 80. The interference signal relates to the moving amount of the mirror 70, and the interference occurs when there is no difference in optical path length between the test light and the reference light. Since the test light is partially reflected on each surface of the container and each surface of the test object 50, a plurality of interference signals is detected as the movable mirror moves. Distances among peaks of these interference signals correspond to the optical path lengths (optical distances) among respective surfaces.

The sum Z1 of the optical path length of the test object 50 and the optical path length of the first medium 60 in the first container corresponds to a sum of three optical path lengths between the back surface of the side 40a and the front surface of the test object 50, between the front surface of the test object and the back surface of the test object 50 (corresponding to the thickness of the test object 50), and between the back surface of the test object 50 and the front surface of the side 40b.

In other words, it corresponds to the optical path lengths of the reflected light fluxes illustrated in FIG. 1 (or the reflected light flux on the back surface of the side 40a and the reflected light flux on the front surface of the side 40b). The interference signal to be measured results from the reflected light fluxes illustrated by the arrows in FIG. 1 and it is unnecessary to detect the interference signals resulting from the reflected light fluxes on the test object 50. Therefore, whether or not the test object 50 tilts does not matter. Any detected interference signals resulting from the test object 50 may be ignored.

The sum $Z_1$ of the optical path length of the first medium 60 may be expressed as follows:

$$Z_1 = N_g(\lambda_c)L + n_{g1}(\lambda_c)(L_1 - L) \qquad \text{Expression 2}$$

Herein, $N_g(\lambda_c)$ denotes the group refractive index of the test object 50, $n_{g1}(\lambda_c)$ denotes the group refractive index of the first medium 60, and these refractive indices are expressed as a function of a wavelength. "L" denotes a geometric thickness of the test object 50 in the light transmitting direction. "$L_1$" denotes a geometric distance between the back surface of the side 40a and the front surface of side 40b of the first container 40, which is a surface interval between a pair of surfaces of the first container 40 sandwiching the test object 50 in the light transmitting direction, and has a known value in this embodiment. Alternatively, $L_1$ may be measured before the first medium is poured in the first container 40 or after the test object 50 and the first medium 60 are taken out of the first container 40.

Next, the test object 50 is taken out of the first medium 60 (first container 40) (S40). The second measuring step is performed which introduces the light into an area that includes the first medium but does not include the test object and measures the optical path length $Z_{10}$ of the first medium 60 (S50). The optical path length $Z_{10}$ is an optical path length between the back surface of the side 40a and the front surface of the side 40b in the first medium 60. When the first medium is air, the optical path length $Z_{10}$ corresponds to $L_1$ multiplied by the air's group refractive index.

The optical path length $Z_{10}$ of the first medium 60 is expressed as follows:

$$Z_{10} = n_{g1}(\lambda_c)L_1 \qquad \text{Expression 3}$$

Next, the first container 40 is replaced with the second container 41 filled with the second medium 61, and the test object 50 is inserted into the second medium (S60). This embodiment replaces the first container 40 with the other container 41, but may replace the first medium 60 in the first container 40 with the second medium 61. At this time, the first container 40 serves as the second container. Utilizing the fact that the medium's refractive index changes as the medium's temperature changes, the second medium may be the first medium having a different temperature.

Next, similar to S20, the test object 50 is centered (S70). S70 may be omitted if a centering shift of the test object 50 is small.

Next, similar to S30, a third measuring step is performed which measures a sum $Z_2$ of the optical path length of the test object 50 and the optical path length of the second medium 61 in the second container (S80). The sum of the optical path length in the second medium is expressed by Expression 4:

$$Z_2 = N_g(\lambda_c)L + n_{g2}(\lambda_c)(L_2 - L) \qquad \text{Expression 4}$$

Herein, $n_{g2}(\lambda_c)$ is a group refractive index of the second medium 61, and "$L_2$" denotes a geometric distance between the back surface of the side 41a and the front surface of side 41b of the second container 41, which is an interval between a pair of surfaces of the second container 41 sandwiching the test object 50 in the light transmitting direction, and has a known value in this embodiment, similar to $L_1$. When the first container is the same as the second container in S60, $L_2$ is equal to $L_1$.

Subsequently, similar to S50, the test object is taken out of the second medium 61 (second container 41) (S90). Then, a fourth measuring step is performed which introduces the light into an area that includes the second medium 61 but does not include the test object 50 in the second container and measures the optical path length $Z_{20}$ of the second medium 61 (S100). The optical path length $Z_{20}$ is an optical path length between the back surface of the side surface 41a and the front surface of the side surface 41b in the second medium 61, and expressed by Expression 5:

$$Z_{20} = n_{g2}(\lambda_c)L_2 \qquad \text{Expression 5}$$

Finally, the refractive index of the test object 50 is calculated based on the measured optical path lengths $Z_1$, $Z_{10}$, $Z_2$, and $Z_{20}$, the known surface interval $L_1$ of the first container 40, and the known surface interval $L_2$ of the second container 41 (S110). Herein, "$L_1$" is an interval of the first medium in the light transmitting direction of the optical path of the light. "$L_2$" is an interval of the second medium in the light transmitting direction of the optical path of the light. The calculating step of S110 deletes (separates) L, $n_{g1}(\lambda_c)$, and $n_{g2}(\lambda_c)$ based on Expressions 2 to 5, and calculates the group refractive index $N_g(\lambda_c)$ of the test object 50 without using thickness information of the test object 50 using the following expression.

Since the thickness information of the test object 50 is not used, even when the test object tilts, the measurement can be realized. In addition, the refractive index of the lens is relatively lowered by the medium. Thus, even when the test object is a lens having a power, the measured wavefront is approximately plane and thus the refractive index of the test object can be highly precisely measured.

$$N_g(\lambda_c) = \frac{(Z_1 - Z_{10})n_{g2}(\lambda_c) - (Z_2 - Z_{20})n_{g1}(\lambda_c)}{(Z_1 - Z_{10}) - (Z_2 - Z_{20})} \qquad \text{Expression 6}$$

$$= \frac{(Z_1 - Z_{10})Z_{20}L_1 - (Z_2 - Z_{20})Z_{10}L_2}{[(Z_1 - Z_{10}) - (Z_2 - Z_{20})]L_1 L_2}$$

The thickness L of the test object 50, the refractive index $n_{g1}(\lambda_c)$ of the first medium, and the refractive index $n_{g2}(\lambda_c)$ of the second medium are given as follows:

$$L = \frac{[(Z_1 - Z_{10}) - (Z_2 - Z_{20})]L_1 L_2}{Z_{20}L_1 - Z_{10}L_2} \qquad \text{Expressions 7}$$

$$n_{g1}(\lambda_c) = \frac{Z_{10}}{L_1}$$

$$n_{g2}(\lambda_c) = \frac{Z_{20}}{L_2}$$

The group refractive index $N_g(\lambda_c)$ obtained by Expression 6 is a group refractive index of the test object 50 for the central wavelength of the light source 10. The phase refractive index $N_p(\lambda_0)$ for another wavelength can be found using a known dispersion curve of a glass material of the test object. The phase refractive index $N_{p0}(\lambda_0)$ is obtained by Expression 8 where $N_{p0}(\lambda_0)$ is a literature value of a phase refractive index for a target wavelength $\lambda_0$ and $N_{g0}(\lambda_0)$ is a literature value of a group refractive index for the central wavelength $\lambda_c$ of the light source 10:

$$N_p(\lambda_0) = N_g(\lambda_c) + \frac{1}{A}(N_g(\lambda_c) - 1) \qquad \text{Expressions 8}$$

$$A = \frac{N_{g0}(\lambda_c) - 1}{N_{p0}(\lambda_0) - N_{g0}(\lambda_c)}$$

The group refractive index $N_g(\lambda_c)$ and phase refractive index $N_p(\lambda_0)$ obtained by Expressions 6 and 8, respectively, are refractive indices to vacuum or absolute refractive indices. In order to turn them into relative refractive indices to air, $N_g(\lambda_c)$ and $N_p(\lambda_0)$ may be corrected by the air's refractive index. Alternatively, the container's surface intervals $L_1$ and $L_2$ may be turned from the geometric distances to the optical distance values and substituted for Expression 6.

This embodiment measures the test light reflected on the back surface of the side 40a and the test light reflected on the front surface of the side 40b, as illustrated in FIG. 1. Alternatively, light reflected on another surface may be used as long as it sandwiches the test object 50.

For example, the light reflected on the front surface of the side 40a and the light reflected on the back surface of the side 40b of the container 40 may be used. At that time, the optical path lengths expressed by Expressions 2 to 5 become larger by amounts corresponding to the optical path lengths (optical thicknesses) of the sides 40a and 40b of the container 40. However, when the optical path lengths (optical thicknesses) of the sides 40a and 40b of the container are separately measured, the optical path length obtained based on Expressions 2 to 5 may be corrected by subtracting it by the amounts of the optical path lengths of the sides of the container. In particular, when the refractive index of the side of the container is approximately equal to the refractive index of the medium, the refractive index on the interface between them becomes very small and thus the measurement of the interference signal becomes difficult. In this case, utilization of another surface is effective as discussed above. For highly precise measurements of the optical path length, two surfaces for which the optical path lengths are measured may be flat surfaces.

In Expression 6, a denominator is made by subtracting a difference between a sum of the optical path length of the test object 50 and the optical path length of the second medium 61 and the optical path length of the second medium 61 from a difference between a sum of the optical path length of the test object 50 and the optical path length of the first medium 60 and the optical path length of the first medium 60. Hence, when the refractive index of the first medium 60 is approximately equal to that of the second medium 61, the denominator becomes very small. When the denominator is very small, the influence of the measurement error of each of the group refractive indices $n_{g1}(\lambda_c)=Z_{10}/L_1$ and $n_{g2}(\lambda_c)=Z_{20}/L_2$ of each medium on the numerator increases, and the calculating precision of the group refractive index $N_g(\lambda_c)$ lowers. For highly precise measurements, a refractive index difference between the media may be made larger.

This embodiment utilizes the SLD as a light source having a broad wavelength band, but may utilize a pulsed laser or a white light source, such as a halogen lamp.

This embodiment uses the low coherent interferometry to measure the optical path length. Instead, the distance measuring technology may be used, such as time-of-flight, a phase-difference detecting method, and a dichroic method.

As discussed above, the measuring method of this embodiment measures a sum of the optical path length of the test object and the optical path length of each of the two types of media having different refractive indices by arranging the test object in the medium and the optical path length of the medium in which the test object is removed from the optical path. The measurements of the optical path lengths are made only by measuring the reflected light reflected on the flat surfaces that sandwich the test object rather than the reflected light reflected on the curved surface of the test object. Since the reflected light reflected on the test object does not have to reach the detector, this embodiment does not have to strictly adjust the gradient of the test object, and thus provides quick measurements. In addition, the reflected light reflected on the flat surface is not affected by the influence of the curvature of the refractive surface, and this embodiment can provide highly precise measurements since the S/N of the interference signal is large. Therefore, the measuring method of this embodiment can highly precisely and quickly measure the refractive index of the test object.

Second Embodiment

Figure 3:
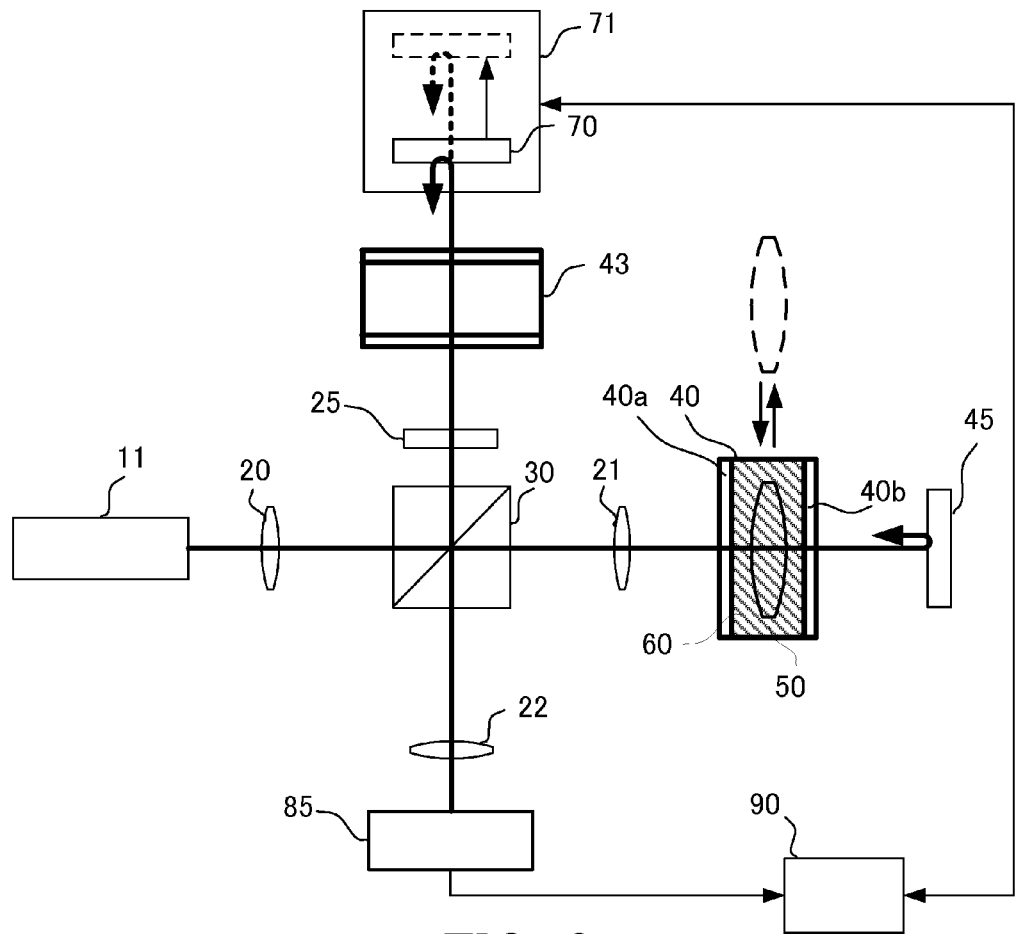
FIG. 3 is a block diagram of a measuring apparatus according to a second embodiment.

FIG. 3 is a block diagram of a measuring apparatus of this embodiment, and those elements in this embodiment which are the same as corresponding elements in the first embodiment will be designated by the same reference numerals. The test object 50 of this embodiment is a lens having a positive power but may be a flat plate, similar to the first embodiment.

The measuring apparatus of this embodiment includes a spectrometer 85 configured to analyze the interference signal in a spectral range, and to detect the spectral band intensity of the interference light instead of the detector 80, and the computer 90 obtains the detection result (measurement result) from the spectrometer 85. In addition, the measuring apparatus of this embodiment makes the side 40b of a transparent material, provides the mirror 45 behind it, and arranges a compensating plate 25 and a container 43 between the beam splitter 30 and the movable mirror.

The first container 40 is configured to house the first medium 60, such as water, and the test object 50. The test object 50 can be inserted into and removed from the first container 40, as illustrated by dotted arrows. The sides 40a and 40b of the first container 40 are made of transparent materials, and the mirror 45 sits behind the container 40. The mirror 45 may serve as the side 40b of the first container 40. The first medium 60 may be replaced with the second medium, such as oil, having a refractive index different from that of the first medium 60.

The light source 11 is a light source having a broad wavelength band, such as a super continuum light source. The light emitted from the light source is collimated by the lens 20, and then split into the transmitting light and reflected light by the beam splitter 30.

The light that has transmitted through the beam splitter 30 passes the lens 21, and enters the first container 40. The light that has entered the first container 40 transmits through the first medium 60 and the test object 50, and then is reflected on the mirror 45. The reflected light is returned to the beam splitter 30, and partially reflected there. Part of the light passes the lens 22, and reaches the spectrometer 85. Similar to the first embodiment, the light that passes the above optical path will be referred to as test light.

The light reflected on the beam splitter 30 passes the compensating plate 25 configured to compensate the dispersion of the lens 21 on the test light side. The compensating plate 25 is made of the same glass material as that of the lens 21, and as thick as the lens 21. The light that passes the compensating plate 25 transmits through the container 43 configured to compensate for the dispersions of the sides 40a and 40b of the container 40 on the test light side.

The container 43 has the same shape as that of the container 40, and is made of the same material as that of the container 40. The light that transmits through the container 43 is reflected on the mirror 70 (movable mirror) on the stage configured to move in the optical axis direction. Thereafter, the light is returned to the beam splitter 30, partially transmits through the beam splitter 30, passes the lens 22, and reaches the spectrometer 85. Similar to the first embodiment, the light passing the above optical path will be referred to as reference light.

When the test object 50 and the medium 60 are not inserted into the container 40 or the container 40 is vacant, the compensating plate 25 and the container serve to make zero the optical path length difference between the test light and the reference light for each wavelength. The compensating plate 25 and the container 43 may be replaced with another member as long as it has the above function. For example, when the lens 21 and the side of the container 40 are made of the same glass material, a thickness of one plate of the same glass material is adjusted and may be used as a substitute.

Figure 4:
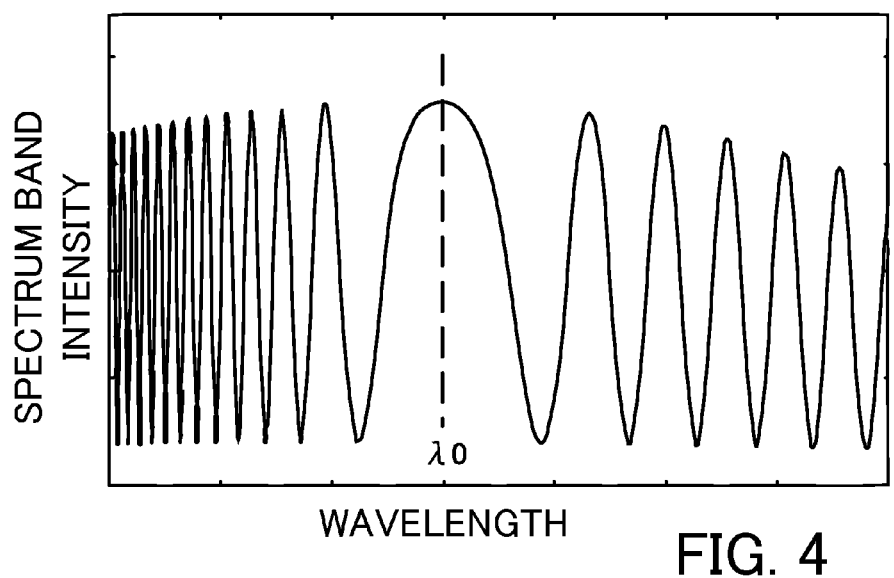
FIG. 4 is a graph of an interference signal obtained by a spectrometer illustrated in FIG. 3 according to the second embodiment.

The interference between the test light and the reference light is detected as an interference signal by the spectrometer 85. FIG. 4 is a graph illustrating the interference signal detected by the spectrometer 85 where the horizontal axis denotes a wavelength, and the vertical axis denotes the spectral band intensity. This interference signal relates to a moving amount of the mirror 70, and $\lambda_0$ changes as the mirror 70 moves. In this embodiment, the mirror 70 is moved so that the $\lambda_0$ can provide a wavelength of the refractive index to be measured.

In calculating the refractive index of the test object 50, the first medium 60 is filled in the first container 40 and the test object 50 is inserted into the first medium (S10), and the test object 50 is centered (S20). Next, a sum $Z_1$ of the optical path length of the test object 50 and the optical path length of the first medium 60 is measured (S30). Expressions 9 express the interference signal for each wavelength.

$$I(\lambda) = I_0[1 + \gamma(\lambda)\cos\phi(\lambda)]$$

$$\phi(\lambda) = \frac{2\pi}{\lambda}[N_p(\lambda)L + n_{p1}(\lambda)(L_1 - L) - n_{pa}(\lambda)L_1 - n_{pa}(\lambda)\delta] \times 2$$

Expressions 9

Herein, $I(\lambda)$ denotes interference intensity, $I_0$ denotes a sum of the intensity of the test light and the intensity of reference light, $\gamma(\lambda)$ denotes visibility, $\phi(\lambda)$ denotes a phase difference between the test light and the reference light, $N_p(\lambda)$ denotes a phase refractive index of the test object, $n_{p1}(\lambda)$ is a phase refractive index of the first medium, $n_{pa}(\lambda)$ is a phase refractive index of air. Similar to the first embodiment, $L_1$ is a known value in this embodiment. "$\delta$" denotes a moving amount of the movable mirror, and is set to 0 at a position where the optical path length of the test light is equal to the optical path length of the reference light when the container 40 is vacant.

"$\lambda_0$" is a position at which the variation rate of the phase $\phi(\lambda)$ to the wavelength is 0, and expressed by Expression 10:

$$\left(\frac{\partial \phi}{\partial \lambda}\right)_{\lambda_0} = \frac{4\pi}{\lambda^2}[N_g(\lambda_0)L + n_{g1}(\lambda_0)(L_1 - L) -$$

$$n_{ga}(\lambda_0)L_1 - n_{ga}(\lambda_0)\delta_1]$$

$$= 0$$

Expression 10

Expression 11 is derived from Expression 10 where $n_{ga}(\lambda)$ is the air's group refractive index. $\delta_1$ is a moving amount of the movable mirror corresponding to $\lambda_0$. Herein, the measurable amount $\delta$ multiplied by $n_{ga}(\lambda)$ is set to the sum $Z_1$ of the optical path length of the test object 50 and the optical path length of the first medium 60.

$$Z_1 = n_{ga}(\lambda_0)\delta_1 = N_g(\lambda_0)L + n_{g1}(\lambda_0)(L_1 - L) - n_{ga}(\lambda_0)L_1$$

Expression 11

Next, the test object 50 is taken out of the first medium 60 (S40), and the optical path length $Z_{10}$ of the first medium 60 is measured (S50). When the first medium 60 is filled in the container 40, the phase difference $\phi(\lambda)$ between the test light and the reference light is expressed by Expression 12:

$$\phi(\lambda) = \frac{2\pi}{\lambda}[(n_{p1}(\lambda) - n_{pa}(\lambda))L_1 - n_{pa}(\lambda)\delta] \times 2$$

Expression 12

Similar to S30, the optical path length $Z_{10}$ is expressed by Expression 13 using Expressions 10 and 11 where $\delta_{10}$ denotes a moving amount of the movable mirror corresponding to $\lambda_0$ in S50:

$$Z_{10} = n_{ga}(\lambda_3)\delta_{10} = (n_{g1}(\lambda) - n_{ga}(\lambda))L_1$$

Expression 13

Subsequently, the first medium 60 in the first container 40 is replaced with the second medium (not illustrated) and the test object is arranged in the second medium (S60). Herein, the container 40 serves as the second container.

Next, the test object is centered (S70), and the sum $Z_2$ of the optical path length of the test object 50 and the optical path length of the second medium is measured (S80). Then, the test object 50 is taken out of the second medium (S90), and the optical path length $Z_{20}$ of the second medium is measured (S100). Similar to the first medium, the sum $Z_2$ of the optical path length of the second medium and the optical path length $Z_{20}$ of the second medium are expressed by Expressions 14:

$$Z_2 = N_g(\lambda_0)L + n_{g2}(\lambda_0)(L_2 - L) - n_{ga}(\lambda_0)L_2 Z_{20} = (n_{g2}(\lambda) - n_{ga}(\lambda))L_2$$

Expressions 14

Finally, the refractive index of the test object 50 is calculated based on the measured values $Z_1$, $Z_{10}$, $Z_2$, and $Z_{20}$ and the known distances $L_1$ and $L_2$ between sides of the containers (S110). The expressions are the same as Expressions 6 to 8 of the first embodiment.

This embodiment can also calculate the phase refractive index without using Expression 8. After S110, only the test object 50 is arranged by removing the medium from the container 40, and the interference signal is acquired as illustrated in FIG. 4. The refractive index and the phase difference of the test object 50 are assumed as in Expressions 15. They are substituted for above Expression 9, and direct fitting is performed for the obtained interference signal. At this time, the refractive index $n_{pa}(\lambda)$ of air utilizes a literature value and $L_1$ and $\delta$ are known. Coefficients $A_1$, $A_2$, $A_3$, $A_4$, $A_5$, and $A_6$ are found through the fitting. In other words, the phase refractive index $N_p(\lambda)$ is found:

$$N_p(\lambda) = \sqrt{\begin{array}{l} A_1 + A_2\lambda^2 + A_3\lambda^{-2} + \\ A_4\lambda^{-4} + A_5\lambda^{-6} + A_6\lambda^{-8} \end{array}}$$

$$\phi(\lambda) = \frac{4\pi}{\lambda}[(N_p(\lambda) - n_{pa}(\lambda))L_1 - n_{pa}(\lambda)\delta]$$

Expressions 15

In the fitting, in order to ignore components of $I_0$ and $\gamma(\lambda)$ in the upper equation in Expressions 9, the amplitude of the interference signal of FIG. 4 may be normalized. The normalization turns the upper expression in Expression 9 into a form $(1+\cos(\phi(\lambda)))$, and facilitates the fitting. In addition, the fitting using Expressions 15 applies a form of a Cauchy's dispersion expression to the phase refractive index, but may use a form of a Sellmeier's dispersion expression. When the fitting wavelength range is narrow, a simple function may be used, such as a polynomial function. Only the low orders of the fitting function down to the third terms in the upper expression in Expressions 15 may be used when the wavelength range is narrow.

The above fitting method removes the medium and again measures the interference signal, but may utilize the interference signal measured in the flow of FIG. 2. For example, when the interference signal of the first medium obtained in S30 is used, the lower expression in Expressions 9 may be used instead of the lower expression in Expressions 15. When the phase refractive index $N_{p1}(\lambda)$ of the medium is unknown, the phase refractive index $N_{p1}(\lambda)$ of the medium can be found in the interference signal of S40 by performing similar fitting.

This embodiment utilizes a system of a Michelson interferometer for the low-coherence interferometer, but may use a system of a Mach-Zehnder interferometer. Moreover, while the spectrometer is located at the position of the detector in FIG. 3, the spectrometer may be located just after the light source and used to split light or a photodiode may be located at the position of the detector and used to detect the interference signal for each wavelength. Instead of arranging the spectrometer just after the light source 11, the spectrometer is eliminated and the light source 11 may be replaced with a wavelength variable light source for wavelength scanning.

Third Embodiment

Figure 5:
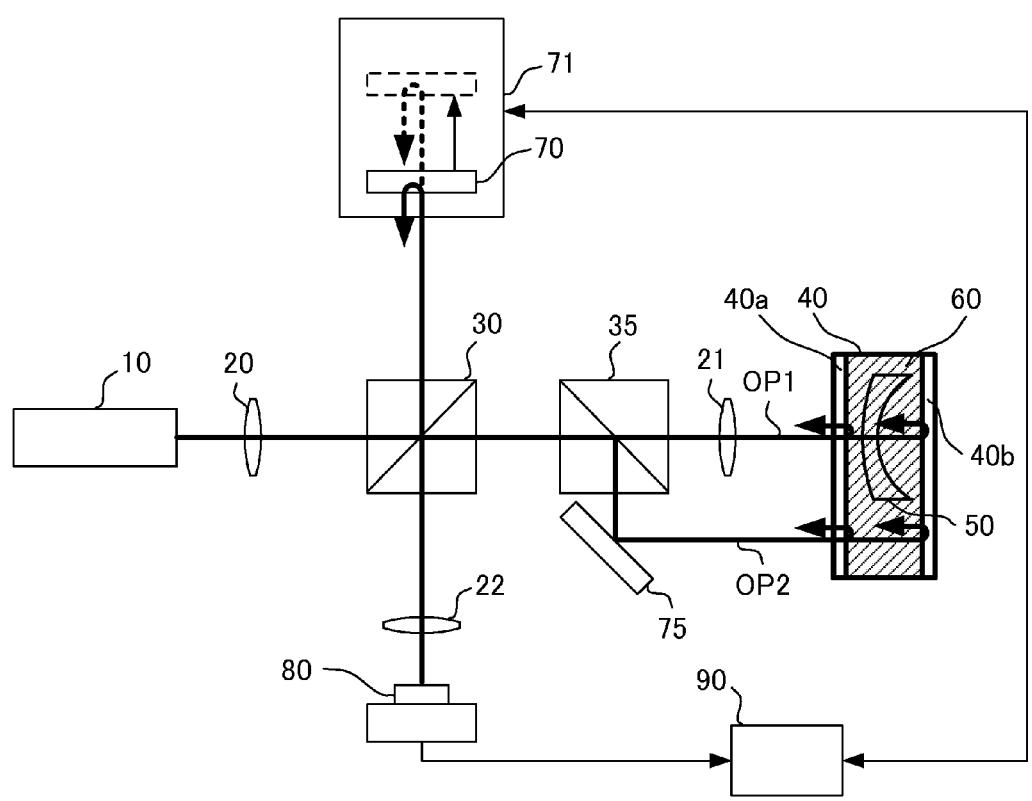
FIG. 5 is a block diagram of a measuring apparatus according to a third embodiment.

FIG. 5 is a block diagram of the measuring apparatus of a third embodiment, and those elements in FIG. 5 which are corresponding elements in the first embodiment are designated by the same reference numerals. The measuring apparatus of this embodiment measures, during one scanning of the mirror 70, both a sum of the optical path length of the medium and the optical path length of the test object while the test object is arranged in each of two types of media having different refractive indices, and the optical path length of the medium in which the test object is not arranged in the optical path, and finds the refractive index of the test object using a measurement results.

The measuring apparatus of this embodiment measures, during one scanning of the mirror 70, both the sum of the optical path length of the test object and the optical path length of the medium in which the test object is arranged in the optical path, and the optical path length of the medium in which the test object is not arranged in the optical path, thereby reduces an error caused by the temperature change of the medium, and shortens a measurement time period.

The measuring apparatus of this embodiment provides the measuring apparatus of the first embodiment with a beam splitter 35 and a deflector mirror 75 so as to split the test light. Thereby, the measuring apparatus of this embodiment can measure, during once scanning of the mirror 70, both the sum of the optical path length of the test object and the optical path length of the medium in which the test object is arranged in the optical path, and the optical path length of the medium in which the test object is not arranged in the optical path.

Similar to the first embodiment, the first container 40 houses the first medium 60 and the test object 50 and the first medium 60 can be replaced with the second medium 61 (not illustrated in FIG. 5). The two media can be replaced with each other while the test object 50 is maintained. Thus, the first container 40 serves as the second container in this embodiment.

The light emitted from the light source 10 is collimated by the lens 20, and then split into the transmitting light (test light) and the reflected light (reference light) by the beam splitter 30. The reference light is reflected on the mirror 70 (movable mirror) on the stage 71, transmits the beam splitter 30, passes the lens 22, and reaches the detector 80.

The test light is split into the transmitting light and the reflected light by the beam splitter 35. The test object 50 and the first medium 60 are arranged on a first optical path OP1 of the test light that transmits through the beam splitter 35. The test light passing the first optical path OP1 is reflected on the sides 40a, 40b of the first container 40, again transmits through the beam splitter 35, is reflected on the beam splitter 30, passes the lens 22, and reaches the detector 80.

The test light reflected on the beam splitter is deflected toward the first container 40 by the deflector mirror 75. The test object 50 is not arranged on a second optical path OP2 of the test light deflected by the deflector mirror 75 and only the first medium 60 is arranged on it. The first optical path OP1 is different from the second optical path OP2, and the incident position of the light introduced into the first medium 60 through the optical path OP1 is different from that through the optical path OP2.

The test light passing along the second optical path OP2 is reflected on the sides 40a, 40b of the first container 40 and then the deflector mirror 75, the beam splitters 35 and 30, passes the lens 22, and reaches the detector 80.

The test light and the reference light sporadically interfere with each other as the mirror 70 moves, and are detected by the detector 80. In this embodiment, each of the test light that passes the first optical path OP1 and is reflected on each surface of the first container 40 and the test light that passes the second optical path OP2 and is reflected on each surface of the first container 40 interferes with the reference light.

Since two test light fluxes split by the beam splitter 35 have different optical paths, the derived interference signals are detected at different positions as the mirror 70 moves. Therefore, the measuring apparatus of this embodiment can measure, during once scanning of the mirror 70, both of the sum of the optical path length of the medium and the optical path length of the test object while the test object is arranged on the optical path, and the optical path length of the medium while the test object is not arranged on the optical path.

In calculating the refractive index of the test object 50, the test object 50 is arranged in the first container 40 and the first medium 60 is filled in the first container 40 (S10), and the test object 50 is centered (S20). Next, both of the sum $Z_1$ of the optical path length of the first medium 60 and the optical path length of the test object 50 and the optical path length $Z_{10}$ of the first medium 60 are measured, during once scanning of the mirror 70 (S30 and S50). Since this embodiment can measure both the optical path lengths $Z_1$ and $Z_{10}$ while the test object 50 is arranged in the first container 40, the step (S40) of taking the test object 50 out of the first medium 60 can be omitted.

Subsequently, without taking the test object 50 out of the first container 40, the first medium 60 is replaced with the second medium (S60). Since only the medium is replaced, the first container 40 serves as the second container. Since the position of the test object is maintained, the centering step (S70) can omitted.

Next, both of the sum $Z_2$ of the optical path length of the second medium and the optical path length of the test object 50 and the optical path length $Z_{20}$ of the second medium are measured, during scanning of the mirror 70 once (S80 and S100). The step (S90) of taking the test object out of the second medium can also be omitted. The group refractive index of the test object may be calculated by using Expression 16.

$$N_g(\lambda_c) = \frac{(Z_1 L_{10} - Z_{10} L_1)Z_{20} - (Z_2 L_{20} - Z_{20} L_2)Z_{10}}{(Z_1 L_{10} - Z_{10} L_1)L_{20} - (Z_2 L_{20} - Z_{20} L_2)L_{10}} \quad \text{Expression 16}$$

Herein, $L_{20}$ is an interval between surfaces that sandwich the first medium in the light transmitting direction, and $L_{20}$ is an interval between surfaces that sandwich the second medium in the light transmitting direction. When the first container 40 has side surfaces parallel to those of the second container or when $L_1 = L_{10}$ and $L_2 = L_{20}$, Expression 16 accords with Expression 6. In addition, since the first container 40 serves as the second container in this embodiment, $L_2 = L_2$ is met.

Figure 6:
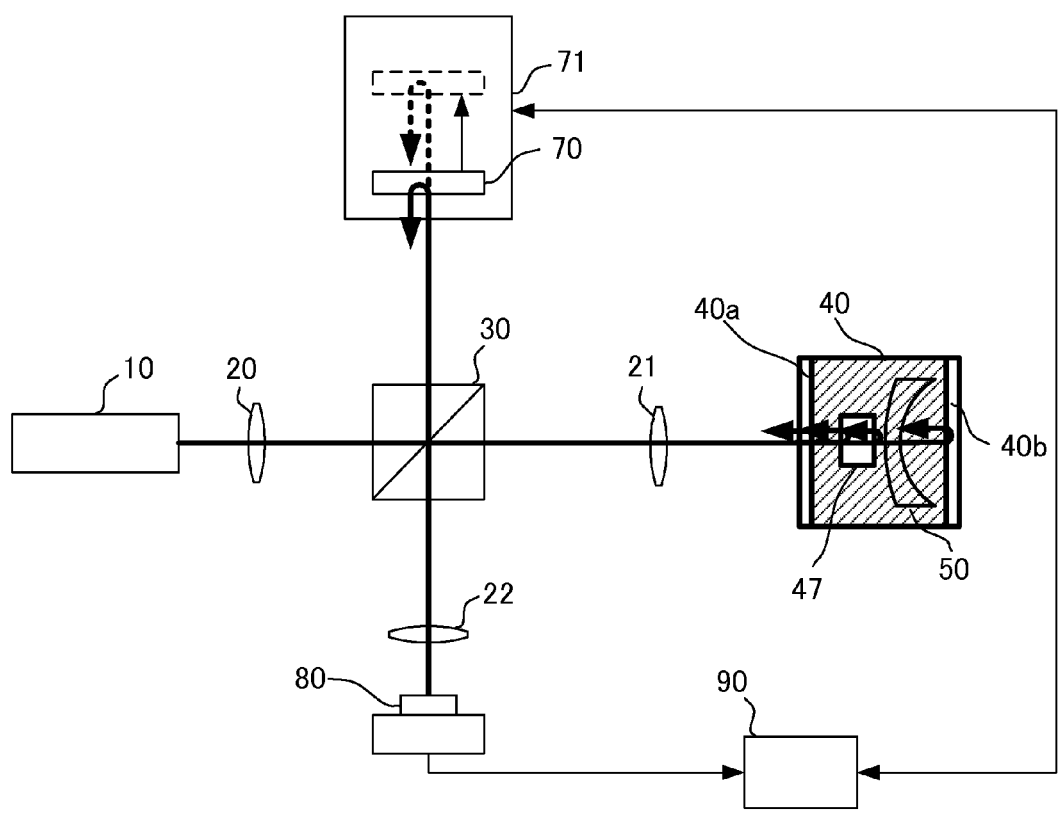
FIG. 6 is a block diagram of a variation of a measuring apparatus illustrated in FIG. 5 according to the third embodiment.

This embodiment adds the beam splitter 35 and the deflector mirror 75 to the measuring apparatus of this first embodiment, as illustrated in FIG. 5, and measures both $Z_1$ and $Z_{10}$ ($Z_2$ and $Z_{20}$) during once scanning of the mirror 70. Alternatively, as illustrated in FIG. 6, a flat plate (transparent member) 47 configured to transmit the light may be inserted into the first container 40, and $Z_1$ and $Z_{10}$ ($Z_2$ and $Z_{20}$) may be measured during one scanning of the mirror 70. In FIG. 6, the optical path length between the back surface of the side 40a and the front surface (incident surface) of the flat plate 47 is $Z_{10}$ ($Z_{20}$), and the interval between the back surface of the side 40a and the front surface (incident surface) of the flat plate 47 is $L_{10}$ ($L_{20}$). The optical path length between the back surface of the flat plate 47 and the front surface of the side 40b is $Z_1$ ($Z_2$), and the interval between the back surface of the flat plate 47 and the front surface of the side 40b is $L_1$ ($L_2$).

Thus, the interval in the first medium along the optical path of the light in the light emitting direction does not always accord with the interval in the second medium along the optical path of the light in the light emitting direction. For example, the interval $L_1$ of the first medium along the optical path in the light transmitting direction in the first measuring step does not always accord with the interval $L_{10}$ of the first medium along the optical path in the light transmitting direction in the second measuring step. Similarly, the interval $L_2$ of the second medium along the optical path in the light transmitting direction in the third measuring step does not always accord with the interval $L_{20}$ of the second medium along the optical path in the light transmitting direction in the fourth measuring step.

When the front surface of the test object 50 is close to a flat surface, the front surface (incident surface) of the test object 50 may be used instead of the flat plate 47, and the second measuring step and the fourth measuring step may utilize the light reflected on the front surface of the test object 50 for measurements.

In that case, the optical path length between the back surface of the side 40a and the front surface of the side 40b is $Z_1$ ($Z_2$), and the interval between the back surface of the side 40a and the front surface of the side 40b is $L_1$ ($L_2$). In addition, the optical path length between the back surface of the side 40a and the front surface of the test object 50 is $Z_{10}$ ($Z_{20}$), and the interval between the back surface of the side 40a and the front surface of the test object 50 is $L_1$ ($L_2$).

As described above, the measuring apparatus of this embodiment can measure both of $Z_1$ and $Z_{10}$ during once scanning of the mirror 70 and both of $Z_2$ and $Z_{20}$ during once scanning of the mirror 70. Since a temperature difference of the first medium in measuring $Z_2$ and $Z_{20}$ and a temperature difference of the second medium in measuring $Z_2$ and $Z_{20}$ can be reduced, the measuring apparatus of this embodiment can highly precisely measure the refractive index of the test object 50. In addition, the number of measuring steps reduces, and a measuring time period can be shortened.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-207647, filed on Sep. 16, 2010 and Japanese Patent Application No. 2011-141527, filed Jun. 27, 2011, which are hereby incorporated by reference herein in their entirety.

What is claimed is:

1. A measuring method comprising:
   a first measuring step of introducing light into a test object and a first medium arranged in a first container and of measuring a sum of an optical path length of the test object and an optical path length of the first medium;
   a second measuring step of introducing the light into an area that includes the first medium but does not include the test object and of measuring the optical path length of the first medium;
   a third measuring step of introducing the light into the test object and a second medium arranged in a second container and of measuring a sum of the optical path length of the test object and an optical path length of the second medium, the second medium having a refractive index different from that of the first medium;
   a fourth measuring step of introducing the light into an area that includes the second medium but does not include the test object and of measuring the optical path length of the second medium; and
   a calculating step of calculating a refractive index of the test object based on the optical path lengths measured in each measuring step and an actual distance of an optical path for which each optical path length is measured in each measuring step.

2. The measuring method according to claim 1, further comprising the steps of:
   taking the test object out of the first container of the first measuring step before the second measuring step; and
   taking the test object out of the second container of the third measuring step before the fourth measuring step.

3. The measuring method according to claim 2, wherein intervals in a light transmitting direction of the light on the optical path in the first medium in each of the first and second measuring steps are equal to each other, and intervals in the light transmitting direction of the light on an optical path in the second medium in the third and fourth measuring steps are equal to each other,
   wherein the calculating step calculates a group refractive index of the test object using the following expression:

$$N_g(\lambda_c) = \frac{(Z_1 - Z_{10})Z_{20}L_1 - (Z_2 - Z_{20})Z_{10}L_2}{[(Z_1 - Z_{10}) - (Z_2 - Z_{20})]L_1L_2},$$

where $N_g(\lambda_c)$ is a group refractive index of the test object for a central wavelength $\lambda_c$ of the light, $Z_1$ is the sum of the optical path length of the test object and the optical path length of the first medium in the first container, $Z_{10}$ is the optical path length of the first medium in the first container when the test object is removed from the optical path of the light, $Z_2$ is the sum of the optical path length of the test object and the optical path length of the second medium in the second container, $Z_{20}$ is the optical path length of the second medium in the second container when the test object is removed from the optical path of the light, $L_1$ is the interval between surfaces of the first container which sandwich the first medium in the light transmitting direction, and $L_2$ is the interval between surfaces of the second container which sandwich the second medium in the light transmitting direction.

4. The measuring method according to claim 1, wherein:
the second measuring step splits the light and introduces split light into the first container using an optical path different from that of the first measuring step while maintaining a position of the test object in the first container in the first measuring step; and
the fourth measuring step splits the light and introduces split light into the second container using an optical path different from that of the third measuring step while maintaining a position of the test object in the second container in the third measuring step.

5. The measuring method according to claim 1, wherein:
the second measuring step utilizes the light reflected on an incident surface of the test object arranged in the first container, and
the fourth measuring step utilizes the light reflected on the incident surface of the test object arranged in the second container.

6. The measuring method according to claim 1, wherein:
the second measuring step utilizes the light reflected on an incident surface of a transparent member arranged between an incident surface of the first container and the test object arranged in the first container and configured to transmit the light, and
the fourth measuring step utilizes the light reflected on the incident surface of the transparent member arranged between an incident surface of the second container and the test object arranged in the second container.

7. The measuring method according to claim 1, wherein the first container is the same as the second container.

8. The measuring method according to claim 1, wherein the calculating step calculates a group refractive index of the test object using the following expression:

$$N_g(\lambda_c) = \frac{(Z_1L_{10} - Z_{10}L_1)Z_{20} - (Z_2L_{20} - Z_{20}L_2)Z_{10}}{(Z_1L_{10} - Z_{10}L_1)L_{20} - (Z_2L_{20} - Z_{20}L_2)L_{10}},$$

where $N_g(\lambda_c)$ is a group refractive index of the test object for a central wavelength $\lambda_c$ of the light, $Z_1$ is the sum of the optical path length of the test object and the optical path length of the first medium in the first container, $Z_{10}$ is the optical path length of the first medium in the first container when the test object is removed from the optical path of the light, $Z_2$ is the sum of the optical path length of the test object and the optical path length of the second medium in the second container, $Z_{20}$ is the optical path length of the second medium in the second container when the test object is removed from the optical path of the light, $L_1$ is an interval between surfaces of the first container which sandwich the test object and the first medium in the light transmitting direction, $L_{10}$ is an interval between surfaces of the first container which sandwich the first medium in the light transmitting direction, $L_2$ is an interval between surfaces of the second container which sandwich the test object and the second medium in the light transmitting direction, and $L_{20}$ is an interval between surfaces of the second container which sandwich the second medium in the light transmitting direction.

9. A measuring apparatus comprising:
a measuring unit configured to introduce light into a test object and a first medium arranged in a first container and to measure a sum of an optical path length of the test object and an optical path length of the first medium, to introduce the light into an area that includes the first medium but does not include the test object and to measure the optical path length of the first medium, to introduce the light into the test object and a second medium arranged in a second container and to measure a sum of the optical path length of the test object and an optical path length of the second medium, and to introduce the light into an area that includes the second medium but does not include the test object and to measure the optical path length of the second medium, the second medium having a refractive index different from that of the first medium; and
a calculator configured to calculate a refractive index of the test object based on optical path lengths measured by the measuring unit and an actual distance of an optical path for which each optical path length is measured.

10. The measuring apparatus according to claim 9, wherein surfaces of the first container which are configured to sandwich the test object are flat surfaces.

11. The measuring apparatus according to claim 9, wherein surfaces of the second container which are configured to sandwich the test object are flat surfaces.

12. The measuring apparatus according to claim 9, wherein:
the measuring unit includes a low-coherence interferometer, and
the low-coherence interferometer includes:
a light source configured to emit low-coherence light;
an interference optical system configured to split the low-coherence light from the light source, to guide split light to the test object and a reference unit, and to enable test light that is the light reflected by surfaces configured to sandwich the test object and the reference light that is the light reflected by the reference unit to interfere with each other; and
a detector configured to detect an intensity of interference light formed by the test light and the reference light.

13. The measuring apparatus according to claim 9, wherein the measuring unit further includes a unit configured to make zero a difference of an optical path length between the test light and the reference light when the first container and the second container are vacant.

* * * * *